US012551347B2

(12) United States Patent
Debbi et al.

(10) Patent No.: US 12,551,347 B2
(45) Date of Patent: Feb. 17, 2026

(54) APPARATUS AND METHOD FOR FORMING A CUSTOM CEMENT-ON-CEMENT ARTICULATING HIP SPACER

(71) Applicant: CEDARS-SINAI MEDICAL CENTER, Los Angeles, CA (US)

(72) Inventors: Eytan M. Debbi, Los Angeles, CA (US); Guy D. Paiement, Los Angeles, CA (US)

(73) Assignee: CEDARS- SINAI MEDICAL CENTER, Los Angeles, CA (US)

(*) Notice: Subject to any disclaimer, the term of this patent is extended or adjusted under 35 U.S.C. 154(b) by 1012 days.

(21) Appl. No.: 17/753,070

(22) PCT Filed: Aug. 17, 2020

(86) PCT No.: PCT/US2020/046697
§ 371 (c)(1),
(2) Date: Feb. 17, 2022

(87) PCT Pub. No.: WO2021/050214
PCT Pub. Date: Mar. 18, 2021

(65) Prior Publication Data

US 2022/0331116 A1 Oct. 20, 2022

Related U.S. Application Data

(60) Provisional application No. 62/898,691, filed on Sep. 11, 2019.

(51) Int. Cl.
*A61F 2/34* (2006.01)
*A61F 2/30* (2006.01)

(52) U.S. Cl.
CPC ............ *A61F 2/30942* (2013.01); *A61F 2/34* (2013.01); *A61F 2002/30677* (2013.01);
(Continued)

(58) Field of Classification Search
CPC .................... A61F 2/30942; A61F 2/34; A61F 2002/30677; A61F 2002/3069; A61F 2002/30957; A61F 2310/00353
(Continued)

(56) References Cited

U.S. PATENT DOCUMENTS 5,630,819 A 5/1997 Ashby
5,879,355 A 3/1999 Ullmark
(Continued)

FOREIGN PATENT DOCUMENTS

FR 2846225 A1 4/2004
RU 82542 U1 5/2009
(Continued)

OTHER PUBLICATIONS

Extended European Search Report for 20862845.3 dated Aug. 28, 2023, 8 pages.
(Continued)

*Primary Examiner* — Eduardo C Robert
*Assistant Examiner* — David C Comstock
(74) *Attorney, Agent, or Firm* — PETERSON IP; Brett Peterson

(57) ABSTRACT

Aspects of the present disclosure include a device for forming a custom cement cast of an acetabular implant for a patient. The device includes an elongated handle, and a head coupled to a proximal end of the elongated handle. The head includes a body, a circumferential lip, and a nipple. The body of the head is shaped as a spherical cap, and includes a circular base and an apex. The circumferential lip extends radially outwardly from the circular base of the body. The nipple extends from the apex of the body in a direction perpendicular to the circular base.

32 Claims, 10 Drawing Sheets

(52) U.S. Cl.
CPC ................. *A61F 2002/3069* (2013.01); *A61F 2002/30957* (2013.01); *A61F 2310/00353* (2013.01)

(58) Field of Classification Search
USPC ..................................... 606/53, 86 R, 91, 92
See application file for complete search history.

(56) References Cited

U.S. PATENT DOCUMENTS

| | | | | |
|---|---|---|---|---|
| 5,997,582 | A * | 12/1999 | Weiss .................. | A61F 2/30756 606/89 |
| 6,162,257 | A | 12/2000 | Gustilo et al. | |
| 8,679,187 | B2 * | 3/2014 | Allen .................... | A61F 2/4684 623/22.24 |
| 9,622,865 | B2 | 4/2017 | Vogt | |
| 2001/0027345 | A1 * | 10/2001 | Merrill .................. | A61F 2/4657 623/908 |
| 2007/0173856 | A1 | 7/2007 | Parker | |
| 2008/0188945 | A1 * | 8/2008 | Boyce ................ | A61B 17/0401 623/23.61 |
| 2010/0185298 | A1 | 7/2010 | Stone | |
| 2014/0188240 | A1 * | 7/2014 | Lang ..................... | A61F 2/3662 29/592 |
| 2016/0015520 | A1 | 1/2016 | Smith et al. | |
| 2017/0290666 | A1 | 10/2017 | Behzadi | |

FOREIGN PATENT DOCUMENTS

| | | | |
|---|---|---|---|
| WO | 2017098039 | A1 | 6/2017 |
| WO | 2021050214 | A1 | 3/2021 |

OTHER PUBLICATIONS

Duncan et al., The role of antibiotic-loaded cement in the treatment of an infection after a hip replacement, Journal of Bone andf Joint Surgery, 1994, 76(11):1742-1751.
Search Report and Written Opinion of International Searching Authority for Application No. PCT/US2020/046697, mailed Nov. 19, 2020 (11 pages).

* cited by examiner

APPARATUS AND METHOD FOR FORMING A CUSTOM CEMENT-ON-CEMENT ARTICULATING HIP SPACER

CROSS-REFERENCE TO RELATED APPLICATIONS

This application is the National Phase of International Application PCT/US2020/046697, filed on Aug. 17, 2020, which designated the United States, which claims priority to and the benefit of U.S. Provisional Patent Application No. 62/898,691, filed on Sep. 11, 2019, each of which is hereby incorporated by reference herein in its entirety.

TECHNICAL FIELD

The present disclosure relates to a device for assisting in orthopedic surgery. Specifically, the disclosure relates to a device for creating a custom cement-on-cement articulating hip spacer during surgery.

BACKGROUND

There are 500,000 total hip arthroplasty procedures in the U.S. annually. The number is expected to rise to over 1 million, due to an aging population. A busy orthopedic surgeon performs ten procedures per day. However, the total hip arthroplasty procedure typically comes with an infection rate of five percent (5%). Infections can be morbid, life-threatening, and costly. Infections can happen due to biofilm growth on a metal implant. Second surgery after an infection comes with more risk and is usually more complicated.

SUMMARY

The standard of care for a chronically infected total hip arthroplasty is removal of all implants and placement of a spacer made of bone cement mixed with antibiotics for a period of time. The cement spacer is a cast created from a mold of a spherical head of a femoral stem. The cement spacer is implanted and articulates with a raw surface of an acetabulum of a patient, which can be very painful. In comparison to a premade antibiotic acetabular and femoral component, the present technology allows for a custom-made cement articulating hip spacer during surgery.

Aspects of the present disclosure include a device for forming a custom cement cast of an acetabular implant for a patient. The device includes an elongated handle, and a head coupled to a proximal end of the elongated handle. The head includes a body, a circumferential lip, and a nipple. The body of the head is shaped as a spherical cap, and includes a circular base and an apex. The circumferential lip extends radially outwardly from the circular base of the body. The nipple extends from the apex of the body in a direction perpendicular to the circular base.

In some aspects, the body of the head is shaped as a hemisphere. In some aspects, the body of the head is shaped to match a prosthetic femoral head fitted for the patient. In some aspects, a radius of the body is sized to match (e.g., modifiable based on) an acetabular defect of the patient. The radius of the body is a radius of an underlying sphere of the spherical cap. In some aspects, the apex is at a pole of the spherical cap. In some aspects, the circumferential lip extends generally along a same plane as the circular base. In some aspects, the nipple is a center of rotation of the device.

In some examples, measurements of the device can include any of the following: the radius of the body is 27.5 mm; the height of the body is 27.5 mm; a radius of the circular base is 55 mm; the circumferential lip extends 5 mm radially outwardly from the circular base; a thickness of the circumferential lip is 5 mm; and a height of the nipple is 5 mm.

In some aspects, the nipple is sized to touch both a cement and an acetabular bone of the patient, thereby forming the custom cement cast. In some examples, the head is co-axially rotatable around the nipple while the cement hardens without disrupting the cement. In some examples, a thickness of the custom cement cast is the same as a height of the nipple. In some examples, a length of the nipple is sized based on an intended thickness of the custom cement cast.

Additional aspects of the present disclosure include a method for treating an infected total hip arthroplasty in a patient. The method includes removing an implant associated with the infected total hip arthroplasty in the patient. A cement is placed in an acetabulum of the patient. A device is pressed into the cement, thereby forming a concave cement acetabular cast. The device is advanced toward an acetabular bone of the patient. The device includes an elongated handle, and a head coupled to a proximal end of the elongated handle. The head includes a body, a circumferential lip, and a nipple. The body is shaped as a spherical cap. The circumferential lip extends radially outwardly from a base of the body. The nipple extends from an apex of the body in a direction perpendicular to the base. The device is advanced until the nipple of the head touches the acetabular bone, thereby ensuring an appropriate thickness of the cement acetabular cast.

In some aspects, the method further includes placing a mineral oil between the cement and the device, thereby preventing the device from adhering to the cement. In some aspects, the method further includes shaping the body of the head to match a prosthetic femoral head fitted for the patient.

In some aspects, the cement includes an antibiotic bone cement. In some aspects, the body of the head is shaped as a hemisphere and includes a circular base. In some aspects, a radius of the body is modifiable based on an acetabular defect of the patient. The radius of the body is a radius of an underlying sphere of the spherical cap. In some aspects, the nipple of the head is a center of rotation of the device. In some aspects, a length of the nipple is modifiable based on the appropriate thickness of the cement acetabular cast. In some aspects, the head is co-axially rotatable around the nipple while the cement hardens without disrupting the cement.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The foregoing and other advantages of the present disclosure will become apparent upon reading the following detailed description and upon reference to the drawings.

Figure 1:
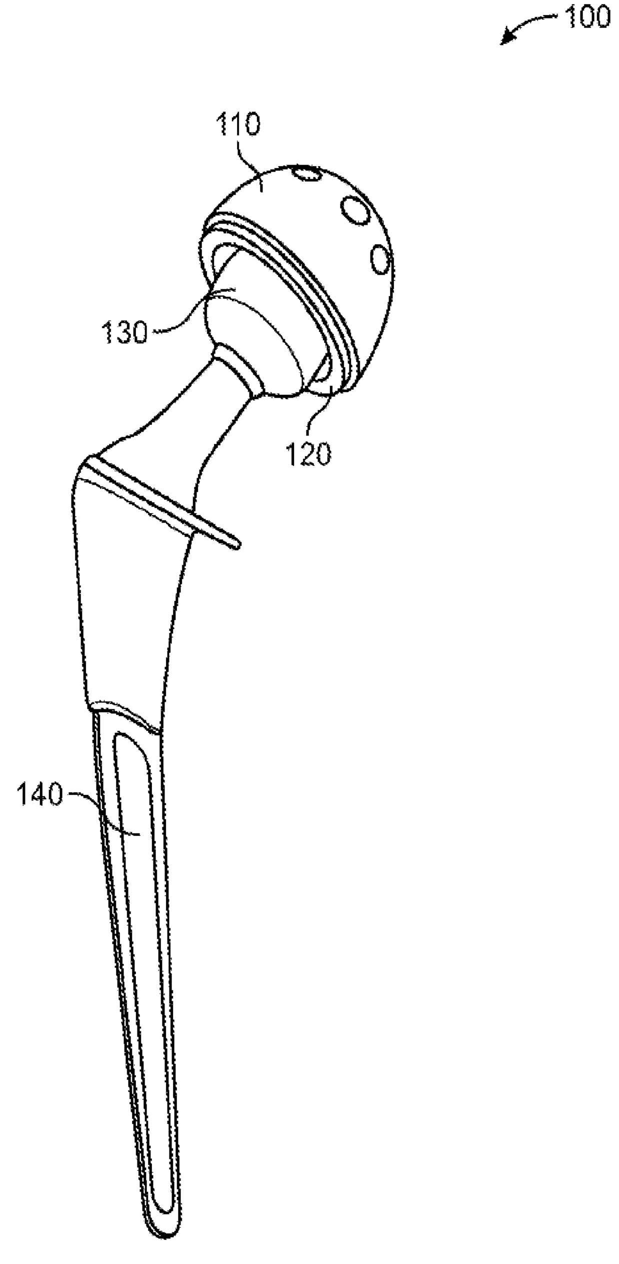
FIG. 1 illustrates a prospective view of an exemplary implant in a total hip arthroplasty, according to some implementations of the present disclosure.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

The present invention is described with reference to the attached figures, where like reference numerals are used throughout the figures to designate similar or equivalent elements. The figures are not drawn to scale, and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

A standard of care for a chronically infected total hip arthroplasty is removal of all implants and placement of a spacer made of bone cement (e.g., poly-methyl-methacrylate) mixed with antibiotics for a period of time (e.g., at least six weeks). A cement spacer is a cast created from a mold of a spherical head on a femoral stem. The cement spacer is implanted and articulates with a raw surface of an acetabulum. The implantation and articulation can be very painful. In comparison to a premade antibiotic acetabular and femoral component, the present technology allows for a custom-made low cost cement articulating hip spacer during surgery. In some examples, the articulating hip spacer is an antibiotic hip spacer.

Figure 2:
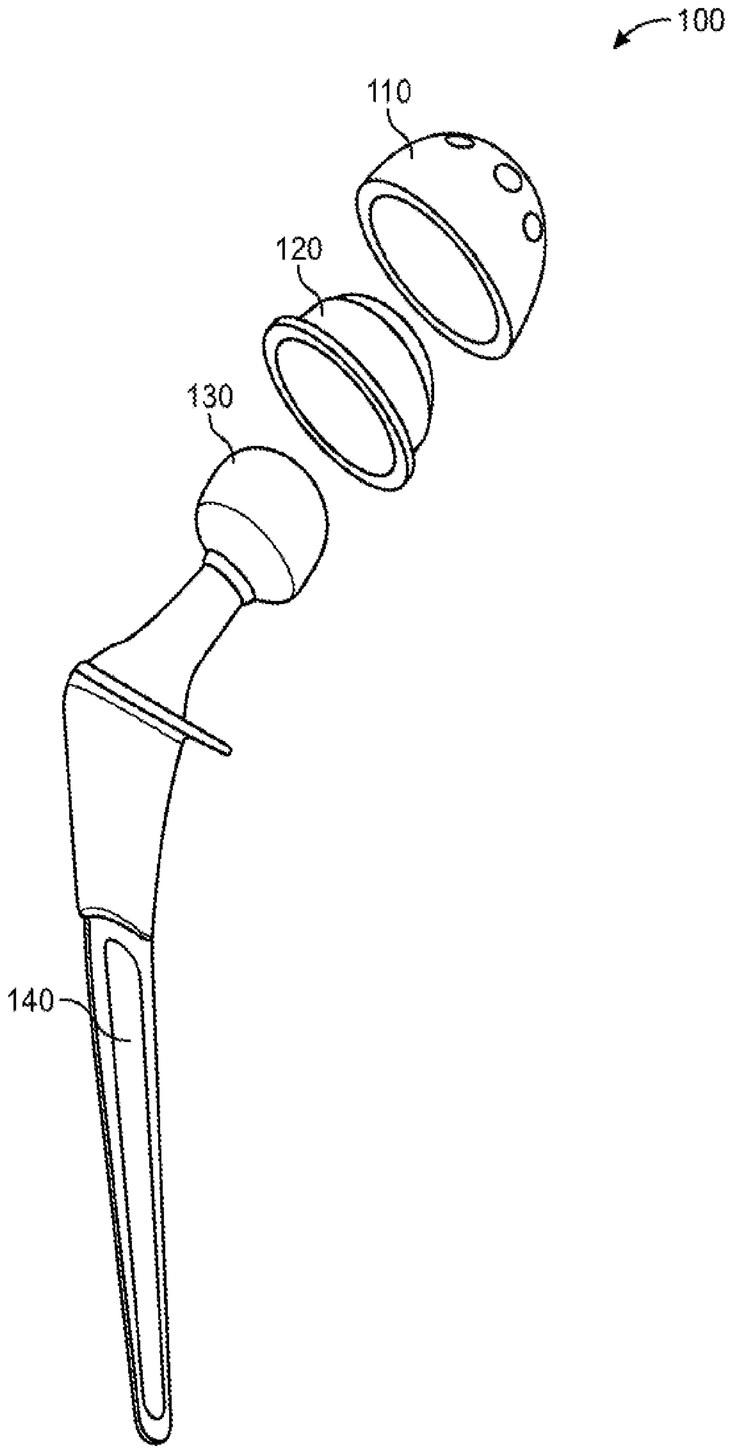
FIG. 2 illustrates an exploded view of the implant of FIG. 1.

In a total hip replacement (e.g., a total hip arthroplasty), damaged bone and cartilage are removed and replaced with prosthetic components, such as an implant 100. Referring generally to FIGS. 1-2, the implant 100 includes a prosthetic cup 110, a liner 120, a prosthetic femoral head 130, and a prosthetic femoral stem 140. In some examples, the prosthetic cup 110, the prosthetic femoral head 130, and the prosthetic femoral stem 140 are made of metal, ceramic, or the like. In some examples, materials used for the implant can also be any kind that can be incorporated into bone, and likely stimulate bone growth onto the implant.

Figure 3:
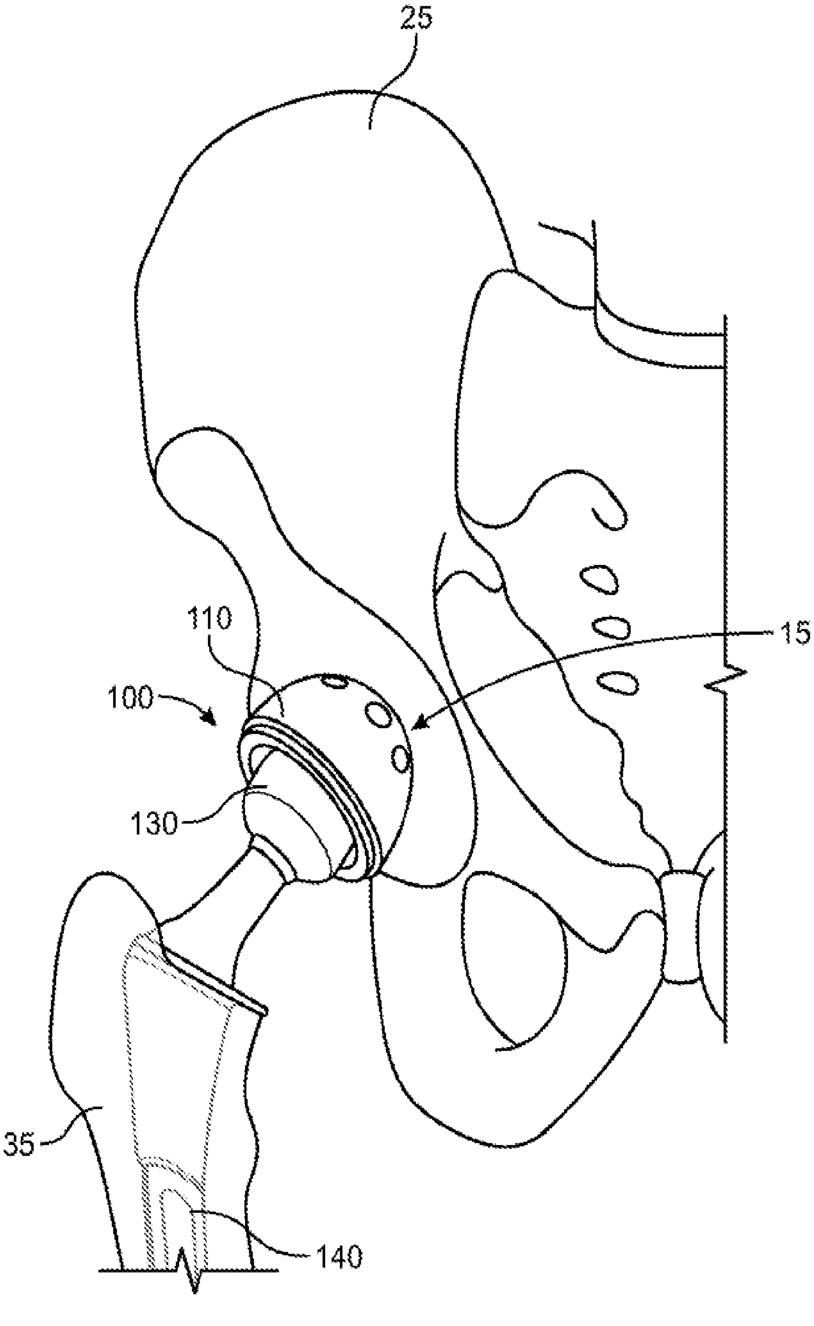
FIG. 3 illustrates a prospective view of the implant of FIG. 1 fitted into a hip of a patient, according to some implementations of the present disclosure.

Referring now to FIG. 3, a damaged femoral head of a patient is removed and replaced with the prosthetic femoral stem 140 inserted into a hollow center of the femur 35. The prosthetic femoral stem 140 may be either cemented or "press fit" into the bone of the femur 35. The prosthetic femoral head 130 is placed on an upper part of the prosthetic femoral stem 140. In some examples, the prosthetic femoral head 130 is in a shape of a ball, and is made of metal or ceramic. The prosthetic femoral head 130 replaces the damaged femoral head that was removed. A damaged cartilage surface of the acetabulum 15 (e.g., a socket in a pelvis of the patient) is removed and replaced with a prosthetic cup 110. The prosthetic cup 110 is held in place with or without screws and rarely cement, and contacts a bone of the acetabulum 15. The liner is inserted between the prosthetic femoral head 130 and the prosthetic cup 110 to allow a smooth gliding surface. In some examples, the liner is made of plastic, ceramic, metal, or the like.

However, the total hip arthroplasty procedure typically comes with an infection rate of five percent (5%). Infections can be morbid, life-threatening, and costly. Infections can happen due to biofilm growth on a metal implant. Second surgery after an infection comes with more risk and is usually more complicated. If an infection occurs and is treated at an early state (usually within six (6) weeks of initial procedure), treatment involves irrigation and debridement, then changing the liner 120 and the prosthetic femoral head 130. Such early state treatment works in 50% to 80% of cases. If an infection recurs or is treated beyond six (6) weeks (e.g., a chronic infection), a standard of care in many countries (such as United States) for treatment is removal of all components and placement of an antibiotic cement spacer.

The current common spacers are one of two options: (1) take out all the components and put in an antibiotic cement mold of a femoral head and a femoral stem; and (2) place a new femoral implant with antibiotic cement around the femoral stem and a new liner with antibiotic cement in the acetabulum. The second option can be a waste of money because the new implant is costly, and must be taken out once the infection is gone.

In addition, treatment for a chronically infected hip replacement can happen in one or two stages. For the one-stage treatment, the infected hip replacement implant is taken out, and a new hip replacement implant is put in. The new hip replacement implant often includes antibiotic bone cement. A downside of the one-stage treatment is a high rate of re-infection, which means expensive components are placed in with a risk of reinfection. For the two-stage treatment, the infected hip replacement implant is taken out, an antibiotic spacer is placed in, and after a waiting period, a new hip replacement implant is then placed. The two-stage treatment is the standard of care in many countries (including United States) and requires two separate procedures. This can be difficult in an already unhealthy patient population. Therefore, an effective and low-cost antibiotic cement spacer of the present disclosure would benefit these patients greatly, especially for the first stage.

In some examples of antibiotic spacers, a metal-on-polyethylene implant is used. This is done by placing cement in the acetabulum and placing a polyethylene component into the cement. Then, instead of a cement spacer, a regular metal femoral head and femoral stem are implanted and held in place with antibiotic cement. There are at least two downsides of this approach. First, new implants increase the cost of the procedure tremendously. Second, metal and polyethylene implants are new foreign surfaces for bacteria to create biofilm—a glycocalyx film that allows bacteria to evade antibiotics and the immune system. In some examples, surgeons can purchase premade cement antibiotic acetabular and femoral components, which allow for cement-on-cement articulation. A downside is that the cost of pre-making such implants can be high, as compared to making a custom cement-on-cement implant during surgery. The reason these options exist is to find methods to protect the acetabulum and/or to prevent pain from cement articulating with bone.

The present disclosure allows a surgeon to create a low-cost custom cement-on-cement articulating antibiotic hip spacer. The present disclosure has several advantages over other solutions. In comparison to metal-on-polyethylene articulating hip spacers, the present disclosure allows for an articulating hip spacer without metal or polyethylene implants. Such metal or polyethylene implants increase the cost of surgery and leave foreign material in an infected wound for potential biofilm formation. In comparison to premade antibiotic acetabular and femoral component, the present disclosure allows for a custom-made low cost solution instead of paying for premade implants. In addition, in some implementations, the present disclosure also allows the surgeon to determine and/or customize the type and/or dosage of antibiotics in the bone cement, which can often be inadequate in premade cement components.

As discussed herein, a typical implant cement spacer can be painful to the patient. The present disclosure allows a physician to mold a cement-on-cement spacer for treatment of infected total hip arthroplasty. The present disclosure forms a cement cast from a mold of an acetabular implant, and allows for the cement-on-cement articulating spacer, thus eliminating the pain of cement articulating with a native acetabulum. The present disclosure includes a device that is inexpensive and aids in reducing patient pain associated with a spacer. In some implementations, the device is a medical device to be used for creating a custom cement-on-cement articulating antibiotic hip spacer during surgery. In some implementations, the device is used in treating infected total hip arthroplasty. The device is a tool and is not implanted in the body during surgery. It is sterilized and re-usable. The device can be made in different sizes, and customizable to the patient. The device's hemispherical head is important to get a correct shape of the resulting spacer, and its nipple is important to get a correct thickness of the resulting spacer.

Figure 4:
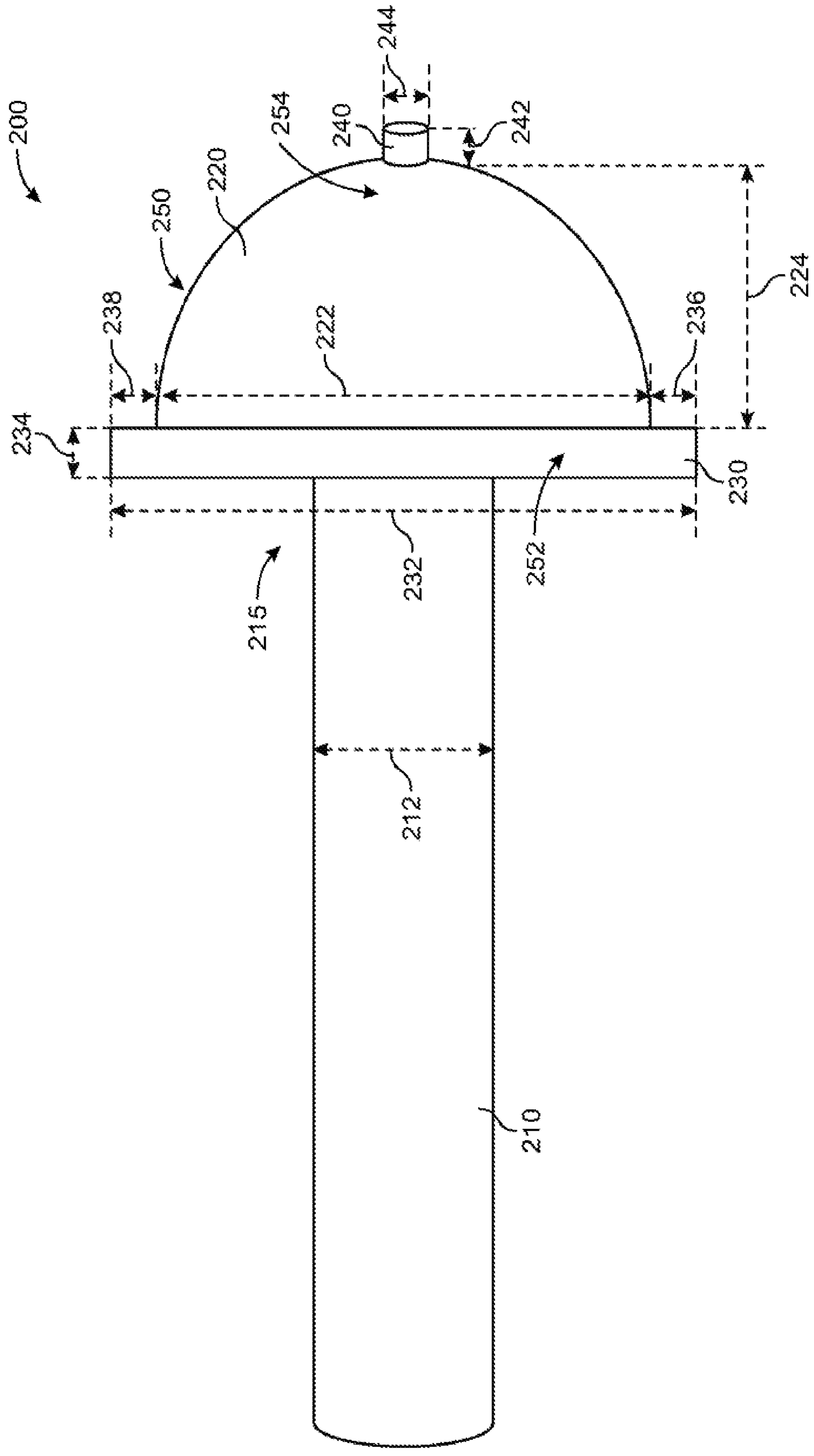
FIG. 4 illustrates a side elevation view of a device for forming a custom cement cast of an acetabular implant for a patient, according to some implementations of the present disclosure.
Figure 5:
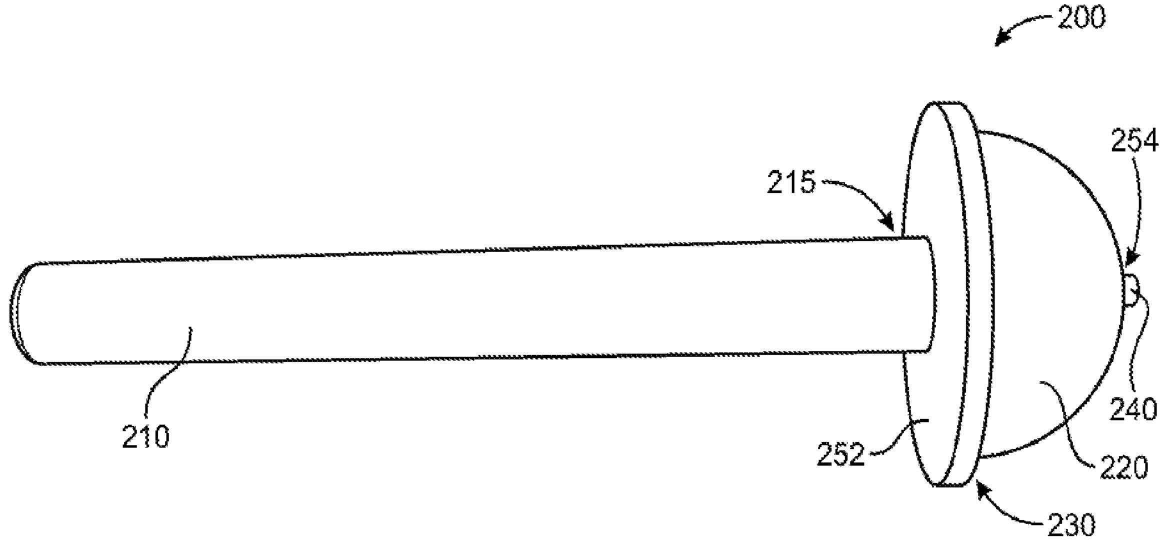
FIG. 5 illustrates a first perspective side view of the device of FIG. 4.
Figure 6:
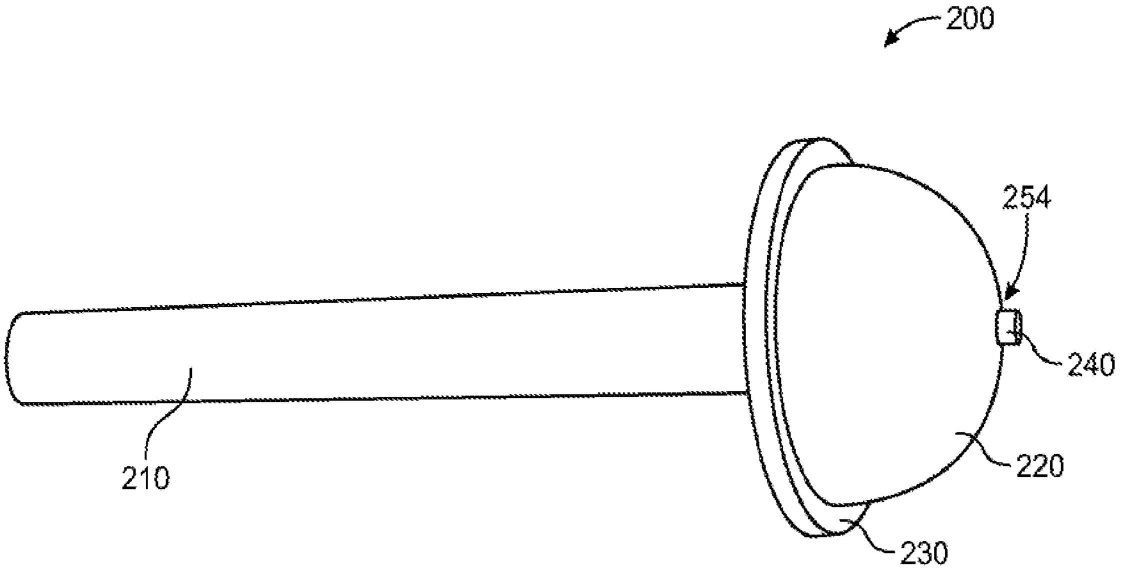
FIG. 6 illustrates a second perspective side view of the device of FIG. 4.

Referring generally to FIGS. 4-6 a device 200 is disclosed herein for forming a custom cement cast of an acetabular implant for a patient. The device 200 includes an elongated handle 210, and a head 250 coupled to a proximal end 215 of the elongated handle 210. The head 250 includes a body 220, a circumferential lip 230, and a nipple 240. The body 220 of the head 250 is shaped as a spherical cap, and includes a circular base 252 and an apex 254. The circumferential lip 230 extends radially outwardly from the circular base 252 of the body 220. The nipple 240 extends from the apex 254 of the body 220 in a direction perpendicular to the circular base 252.

In some aspects, the body 220 of the head 250 is shaped as a hemisphere. In some aspects, the body 220 of the head 250 is shaped to match a prosthetic femoral head fitted for the patient. In some aspects, a radius of the body 220 is sized to match (e.g., modifiable based on) an acetabular defect of the patient. The radius of the body 220 is a radius of an underlying sphere of the spherical cap. In some aspects, the apex 254 is at a pole of the spherical cap. In some aspects, the circumferential lip 230 extends generally along a same plane as the circular base 252. In some aspects, the nipple 240 is a center of rotation of the device 200.

Referring to FIG. 4, a diameter or width 212 of the handle 210 is 20 mm. The body 220 includes a diameter (or width) 222 of 55 mm, a height 224 of 27.5 mm. In the illustrated example where the body 220 is shaped as a special type of spherical cap—a hemisphere—a diameter 222 of the circular base 252 is the same as the diameter 222 of the body 220 (e.g., the diameter of its underlying sphere). However, it is also contemplated that, in other examples, the body 220 is shaped as other types of spherical caps, where the diameter of its underlying sphere is different from the diameter of its circular base.

Furthermore, the circumferential lip 230 includes an average thickness 234 of 5 mm; and the circumferential lip 230 extends 5 mm radially outwardly from the circular base 252. The circumferential lip 230 extends at a distance 236 from a first side of the body 220, and at a distance 238 from an opposite side of the body 220. In some examples, the circumferential lip 230 extends radially outwardly at a uniform distance from all around, therefore the distance 236 and the distance 238 are the same. In some such examples, a total diameter 232 of a disk (including the circular base 252 and the circumferential lip 230) is 65 mm.

In some examples, the nipple 240 is shaped as a short cylinder. The nipple 240 includes a height 242 of 5 mm, and a diameter 244 of 5 mm. In some such examples, a resulting cement cast can have a thickness of about 5 mm due to the height 242 of the nipple.

The specific dimensions of the elements of the device 200 as described herein is only meant as an example. Other dimensions are contemplated according to medical practice. In some aspects, the diameter 222 of the body 220 is modifiable such that different sized molds of an acetabulum (e.g., the acetabulum 15) can be created. According to some implementations of the present disclosure, a set of various sized heads (e.g., hemispheres) each includes a circumferential lip of the same size (e.g., 5 mm). Alternatively, a set of various sized heads each includes a proportionally sized circumferential lip. For example, a head having a 55 mm body includes a 5 mm circumferential lip; a head having a 66 mm body includes a 6 mm circumferential lip, etc.

The set of heads can each have a handle of their own, or alternatively be removably attached to one universal handle. In some examples, the diameters of premade or intraoperatively molded cement femoral heads range from 48 mm to 64 mm. Therefore, the diameters for the hemispheres disclosed herein range from 48 mm to 66 mm. The reason for the large variability in dimension is that the size of the acetabular defect depends on the size of the patient, the previous acetabular component, the bone loss, or any combination thereof. As such, the acetabular defects among patients vary from small defects to large defects. Therefore, one size of device head would not be able to fit all patients. Additionally or alternatively, the hemisphere chosen for the acetabular mold is 1-2 mm larger in diameter than that of the femoral head, such that the femoral head will articulate smoothly in the acetabulum.

Figure 9:
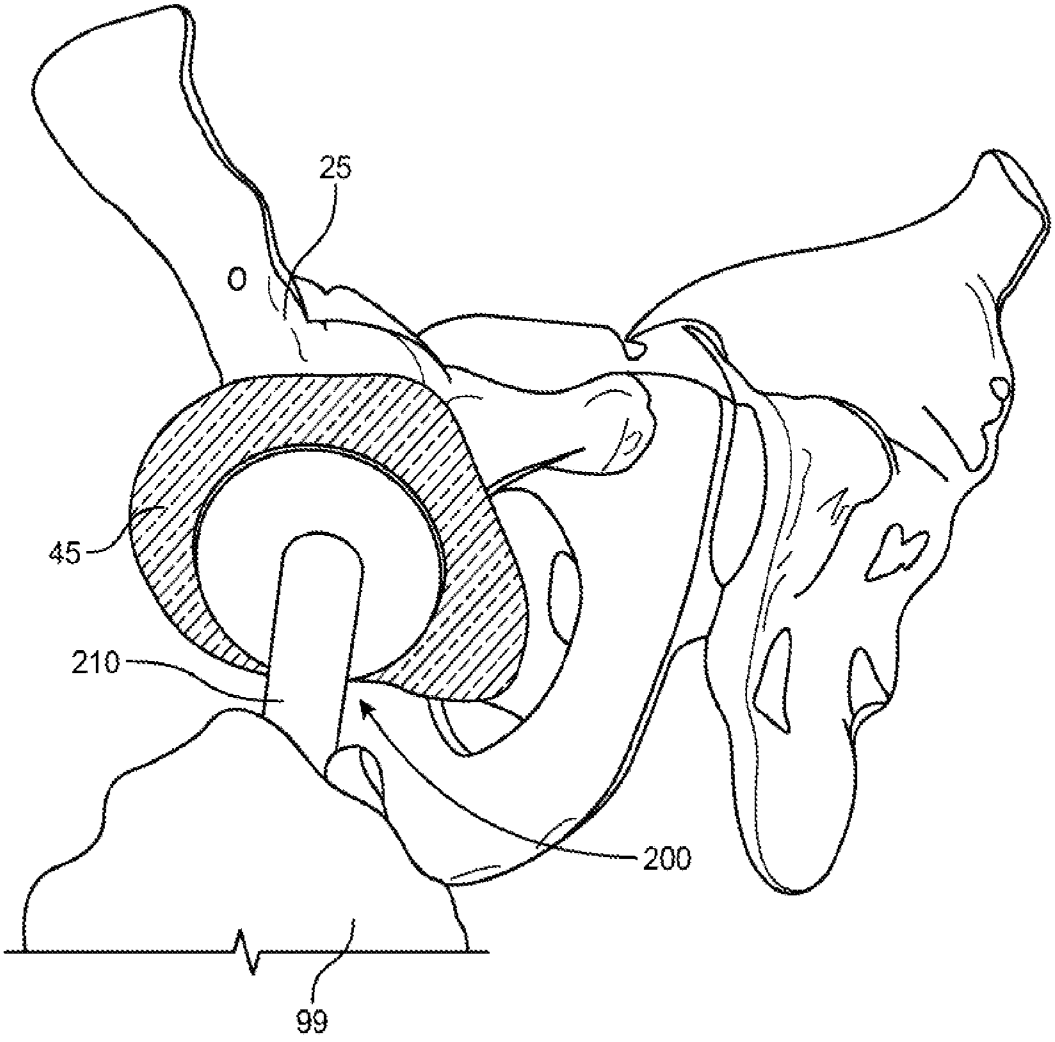
FIG. 9 illustrates a device pressed into the bone cement of FIG. 8 for forming a custom cement cast, according to some implementations of the present disclosure.

In some aspects, the nipple 240 is sized to touch both a cement 45 and an acetabular bone of the patient, thereby forming the custom cement cast (FIG. 9). In some examples, the head 250 is co-axially rotatable around the nipple 240 while the cement 45 hardens without disrupting the cement 45. In some aspects, a thickness of the custom cement cast is the same as a height of the nipple 240. For example, if the height of the nipple is 5 mm, the resulting thickness of the custom cement cast would be about 5 mm. In some aspects, a length of the nipple 240 is sized based on an intended thickness of the custom cement cast. In some examples, the length of the nipple 240 is sized based on an intended acetabular offset from the pelvis the surgeon requires in order to attain appropriate tension and/or stability of the hip joint.

The nipple 240 is also modifiable in dimension. This allows the surgeon to accurately dial in the thickness of the cement mantle required. The thickness is important for several reasons. First, adequate thickness is needed to give enough strength to the cement construct. Second, proper antibiotic elusion requires having sufficient cement. Third, accurate thickness aids in restoring the offset of the center of rotation of the hip. To be more specific on the third point—there is often significant bone loss when a previous acetabular component is removed. A traditional antibiotic spacer articulating with raw bone would have a significantly reduced offset since there is no acetabular component any longer. This reduced offset leads to poor biomechanics of the spacer and can in turn lead to dislocation of the spacer. By creating a mold of an acetabular component, however, the offset can be restored—It is the nipple 240 that allows the surgeon to dial in the amount of offset required.

According to some implementations of the present disclosure, the dimensions of the nipple 240 is further based on the bone loss and/or the natural hip architecture of the patient. For example, the thickness of a standard metal cup (including polyethylene liner) is approximately 10 mm at the apex. Therefore, the height of the nipple 240 to restore just the previous hardware would theoretically be 10 mm; however, a range of nipples from 5 mm to 20 mm in length should be available, taking into consideration the offsets discussed herein. In some examples, the nipple 240 is integral to the body 220. In some other examples, the nipple 240 is removably attached to the body 220 and is therefore interchangeable. Regarding the diameter of the nipple, 5 mm is preferred to create a relatively small defect in the acetabular mold.

According to some implementations of the present disclosure, the nipple 240 is shaped as a cylinder, such that the cement mantle is not disrupted while rotating the device on the nipple axis as the cement hardens. In addition, shaped as a cylinder takes into consideration the required diameter needed to create an adequate mold thickness and to restore offset, while creating a minimal defect in the mold. Although it is contemplated that the nipple 240 can be of other shapes (e.g., a rectangle), a cylinder is generally preferred when rotating the device as the cement hardens.

Figure 7:
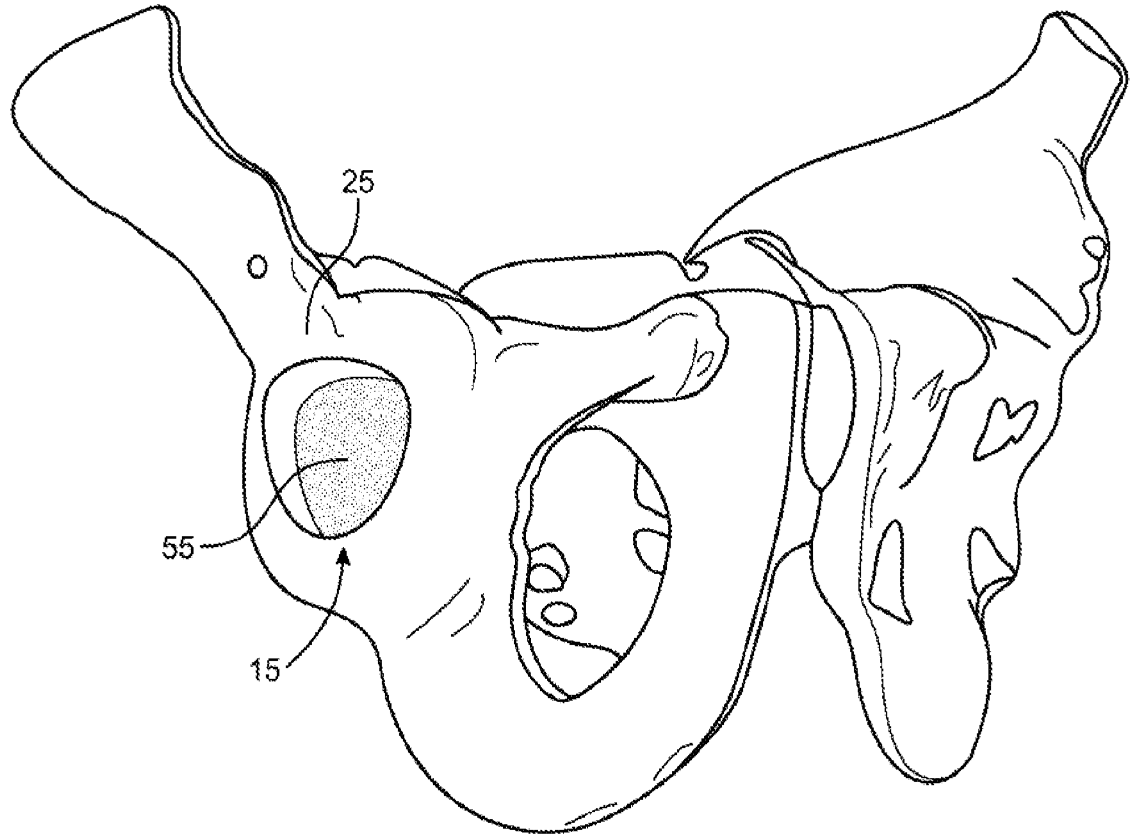
FIG. 7 illustrates a pelvic bone of a patient prior to fitting a custom cement cast of an acetabular implant, according to some implementations of the present disclosure.
Figure 8:
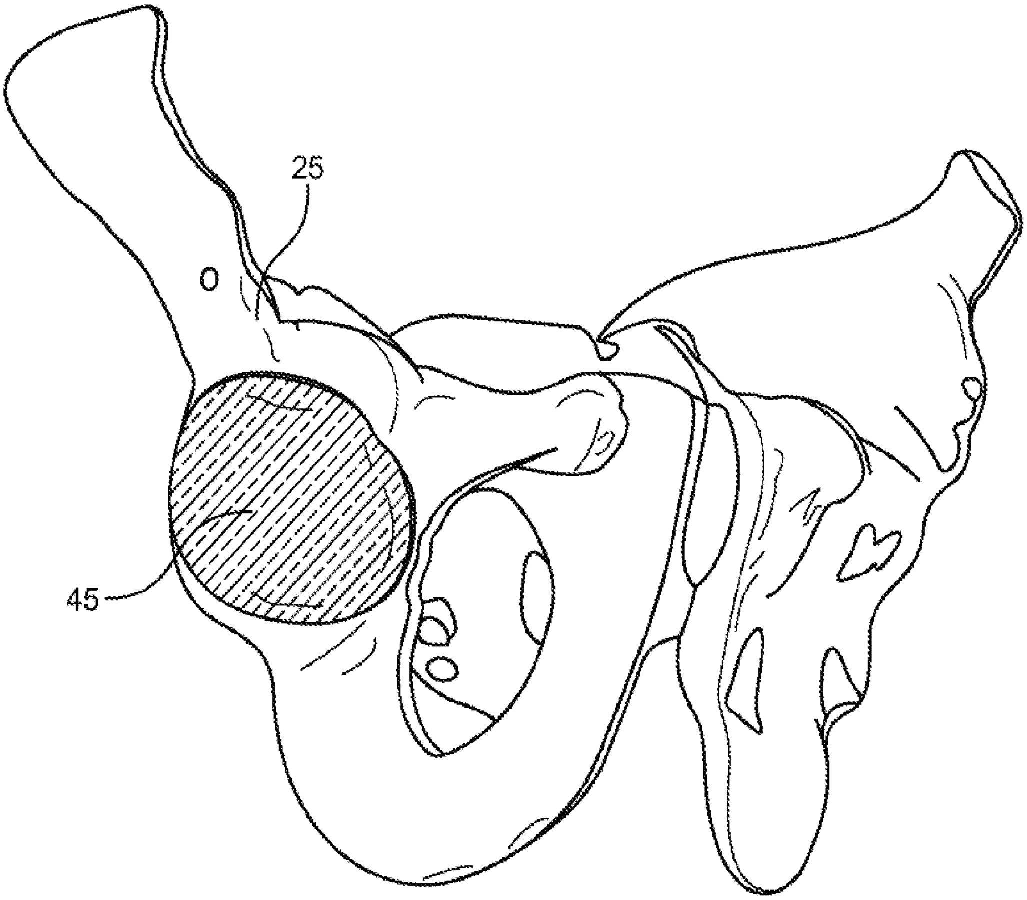
FIG. 8 illustrates a bone cement placed into an acetabulum of the pelvic bone of FIG. 7, according to some implementations of the present disclosure.
Figure 10:
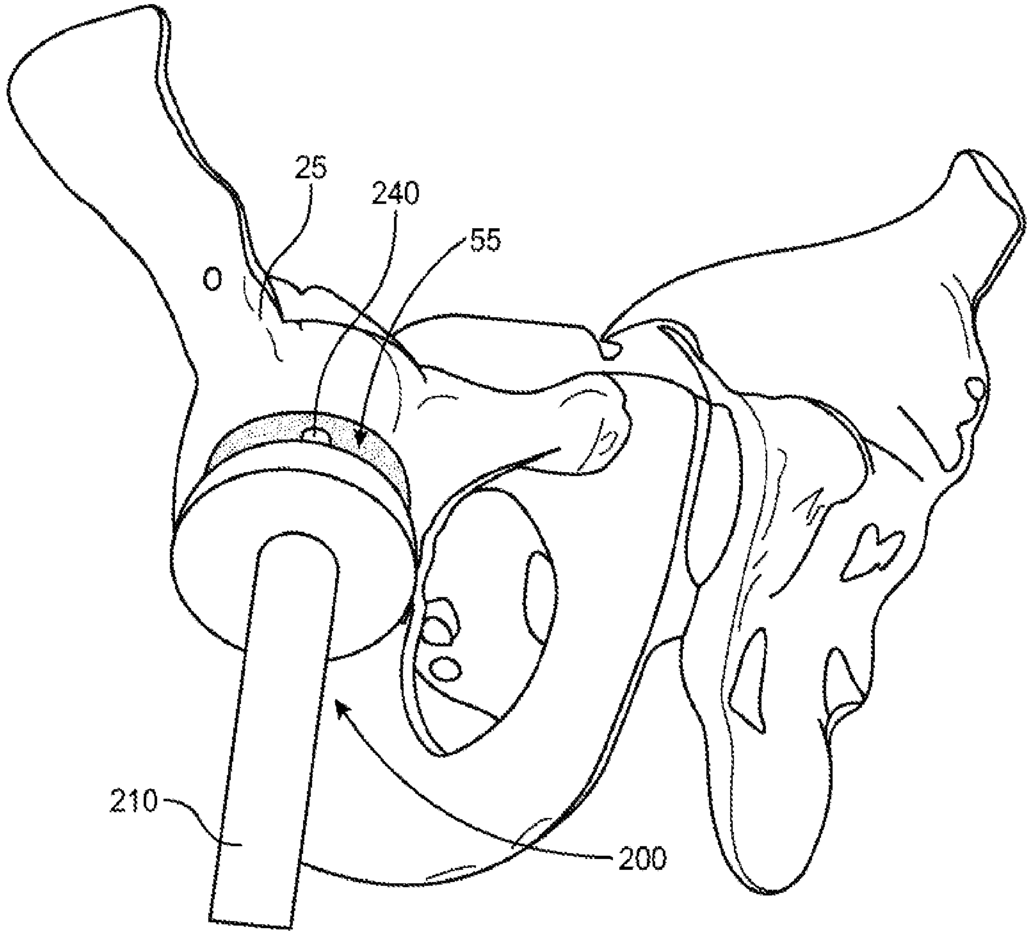
FIG. 10 illustrates a device pressed into an acetabulum of the pelvic bone of FIG. 7 without bone cement, according to some implementations of the present disclosure.
Figure 11:
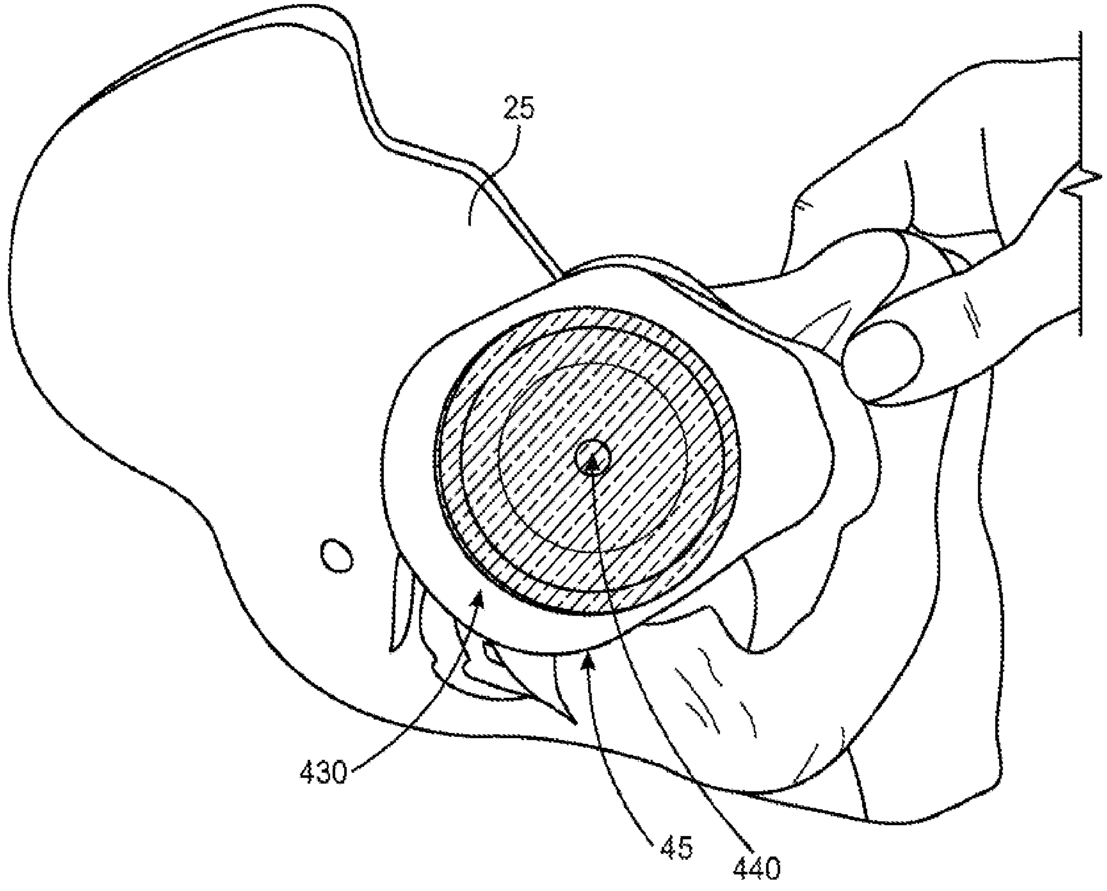
FIG. 11 illustrates a resulting bone cement after the device of FIG. 9 is removed, according to some implementations of the present disclosure.

Additional aspects of the present disclosure include a method for treating an infected total hip arthroplasty in a patient. The method can be illustrated by FIGS. 7-11 of the present disclosure. For example, FIG. 7 illustrates a pelvic bone 25 of a patient prior to fitting a custom cement cast of an acetabular implant; FIG. 8 illustrates a bone cement 45 placed into an acetabulum of the pelvic bone 25 of the patient; FIG. 9 illustrates the device 200 pressed into the bone cement 45 for forming the custom cement cast; FIG. 10 illustrates the device 200 pressed into an acetabulum of the pelvic bone 25 of the patient without bone cement; and FIG. 11 illustrates the resulting bone cement 45 after the device 200 is removed.

The method includes removing an implant associated with the infected total hip arthroplasty in the patient. Referring now to FIGS. 8-9 and 11, a cement 45 (e.g., bone cement) is placed in an acetabulum of the patient. A device 200 (such as the device 200 of FIGS. 4-6) is pressed into the cement 45, thereby forming a concave cement acetabular cast (FIG. 11). The device 200 is advanced toward an acetabular bone of the patient. Such as shown herein with regard to FIGS. 4-6, the device 200 includes an elongated handle 210, and a head 250 coupled to a proximal end 215 of the elongated handle 210. The head 250 includes a body 220, a circumferential lip 230, and a nipple 240. The body 220 is shaped as a spherical cap. The circumferential lip 230 extends radially outwardly from a base 252 of the body 220. The nipple 240 extends from an apex 254 of the body 220 in a direction perpendicular to the base 252.

The device 200 is advanced until the nipple 240 of the head 250 touches the acetabular bone 55, thereby ensuring (i) an appropriate thickness of the cement acetabular cast and/or (ii) an intended acetabular offset from the pelvis. Referring more specifically to FIG. 11, after the device 200 is removed, the concave cement acetabular cast is formed, showing a negative impression 440 of the nipple 240 (e.g., in a shape of a hollow dot), and a negative impression 430 of the circumferential lip 230 (e.g., in a shape of a hollow ring).

In some aspects, the cement includes an antibiotic bone cement. In some aspects, the method further includes placing a mineral oil between the cement 45 and the device 200, thereby preventing the device from adhering to the cement 45. In some aspects, the method further includes shaping the body 220 of the head 250 to match a prosthetic femoral head 250 fitted for the patient.

In some aspects, the body 220 of the head 250 is shaped as a hemisphere and includes a circular base 252. In some aspects, a radius of the body 220 is modifiable based on an acetabular defect of the patient. The radius of the body 220 is a radius of an underlying sphere of the spherical cap. In some aspects, the nipple 240 of the head 250 is a center of rotation of the device 200. In some aspects, a length of the nipple 240 is modifiable based on the appropriate thickness of the cement acetabular cast. In some aspects, the head 250 is co-axially rotatable around the nipple 240 while the cement hardens without disrupting the cement.

In contrast to knee replacement surgeries, determining a cement thickness in a knee is easier because a tibial plateau is exposed in surgery. However, in the hip, the acetabulum 15 is not visible once cement is inserted. Therefore, the nipple 240 the device 200 is critical in determining the thickness 234 of the cement mantle. Furthermore, although there are other ways to determine depth in orthopedic surgery or in other fields (e.g., using a pin, a depth gauze, or a ruler), in the present disclosure it is specifically the fact that there is the nipple 240 at the very apex 254 of the dome of the device 200 that is critical. Placing the nipple 240 at the apex 254 of the dome allows the surgeon to co-axially rotate the handle 210 of the device 200 while the cement 45 hardens without disrupting the cement 45. The modularity of the length of the nipple 240 allows the surgeon to customize a center-of-rotation to the patient to achieve appropriate tension, stability, limb length, and/or offset.

As disclosed herein, in some implementations, the methods and devices of the present disclosure can be used in surgery after a total hip replacement is removed from the patient (e.g., due to infection). The standard of care in many countries (including the United States) is to surgically place a temporary antibiotic bone cement spacer. The present disclosure allows for a unique cement-on-cement spacer by creating a unique acetabular cup made from bone cement. After a total hip replacement is removed, there is a large defect in the patient's acetabulum. The present disclosure addresses this defect. The specific design as well as the ratios and dimensions of the disclosed device are critical to the present disclosure's ability to address this defect. Some critical aspects of the disclosed device are addressed in greater detail throughout this disclosure and as follows.

Shape of the Body 220—the Spherical Cap and the Hemisphere

The disclosed device 200 is configured to generate an acetabular bone cement hemispherical cup. For this reason, the body 220 of the device 200 is in the shape of a spherical cap. This is usually a hemisphere of a certain diameter (e.g., the diameter 222). The acetabular defect shape can vary greatly depending on the bone loss due to infection and/or surgery. Since the ultimate goal is to create an articulating cement-on-cement spacer, the device 200 is configured to create a hemispherical acetabular cup made from bone cement. If the shape is greater than a hemisphere, then a spherical femoral head of similar diameter will not be able to be reduced into this cup. Any less than a hemisphere is possible in some scenarios, but can lead to under-coverage of a spherical femoral head of similar diameter and/or risk dislocation. By being the shape of a hemisphere, the device body 220 will create a cast of a hemispherical concave cement acetabular cup.

Diameter 222 of the Body 220

The size of the acetabular defect can vary greatly depending on the bone loss due to infection and/or surgery. Therefore, the size of the acetabular bone cement cup should be tailored accordingly. The present disclosure allows for customization by the surgeon. First, the diameter of the defect is sized. Then, the disclosed device 200 can be chosen with the appropriately sized diameter 222. For example, there could be several options available in the operating room for the surgeon to choose from. Choosing the appropriate size would also allow the surgeon to fill the defect with the largest and most appropriate acetabular cup, and similarly sized femoral head. Larger femoral heads have a reduced risk of dislocation, and therefore would increase the stability of the cement-on-cement articulating spacer. Considering the anatomy of the acetabulum, the diameters for the hemispheres can range from 48 mm to 66 mm. The reason for the large variability in dimension is that the size of the acetabular defect depends on the size of the acetabular defect.

Nipple 240 and Height 242 of Nipple 240

The nipple 240 is a critical aspect of the device 200. When creating a custom acetabular bone cement cup, the thickness of the cement cup may be determined and/or decided. The nipple 240 is critical for at least the following reasons.

The thickness of the cement at the apex 254 of the custom cement cup determines the offset of the acetabulum, as well as the entire cement-on-cement antibiotic articulating spacer. Offset is an important biomechanical aspect of a hip joint that allows for appropriate loading of the hip and stability of the joint. Offset is often reduced when a total hip replacement is removed and traditional antibiotic bone cement spacers are implanted, since there is no longer any acetabular component in place. Therefore, those traditional spacers have a high risk of dislocation.

In contract, the present disclosure allows for the restoration of the offset, and furthermore dialing in the specific offset that is required for a particular patient. As the offset is increased, the soft tissue tension increases and allows for more stability of the hip. Too much offset creates too much tension, leading to pain and difficulty with motion. Too little offset creates instability of the hip and risk for dislocation. For at least this reason alone, the nipple 240 of the device 200 can be modified in order to dial in the appropriate offset as discussed further herein.

The thickness of the cement of the custom cement cup will also determine the strength of the cement. The thicker the cement mantle, the more resistance to fracture of the cement. If too thick, there is insufficient space to place an appropriately sized femoral head. If too thin, the cement mantle is at risk for fracture. For at least this reason alone, the nipple 240 of the device 200 can be modified in order to dial in the appropriate cement mantle as discussed further herein.

For these reasons, the present disclosure allows for dialing in the cement thickness of the cement cup. In some implementations, adjusting and/or modifying the cement thickness can be carried out using the nipple 240 of the device 200. In some such implementations, the height 242 of the nipple 240 aids in determining the thickness of the cement as follows. First, the thickness of the cement that is required can be determined. Then, the nipple 240 with the appropriate height 242 is chosen. There can be several options available in the operating room. The chosen device 200 is then passed into the soft antibiotic bone cement in order to create the cast of the cement acetabular cup. With the nipple 240 at the apex, the device 200 is pressed into the soft bone cement until the nipple 240 touches the inside of the acetabulum 15 and gives resistance. At this point, the appropriate depth has been achieved. The device 200 can be held in place until the cement hardens.

For example, if the height 242 of the nipple 240 is 5 mm, the resulting thickness of the custom cement cast would be about 5 mm. In uninfected total hip replacements, the thickness of a standard metal cup and liner is approximately 10 mm at the apex. Therefore, to restore the offset of the previous center of rotation of the acetabulum 15, the height 242 of the nipple 240 would need to be about 10 mm. This may change, however, depending on the size of the new acetabulum and femoral head. Therefore, a range of nipples from 5 mm to 20 mm in height can be available in order to decide the exact offset needed.

Circumferential Lip 230 and Diameter 232 of the Circumferential Lip 230

The present disclosure has a circumferential lip 230 that is essential when creating the cement acetabular cup. This circumferential lip 230 exists to ensure that only a hemispherical cup is being created and not a cup that is greater than a hemisphere. Without the circumferential lip 230, as the device 200 is pushed into the soft cement, the cement will displace outward and engulf the device 200, thereby creating a cup that is more than a hemisphere. If the created cup is more than a hemisphere, it is unlikely that the correct size femoral head can be placed into this cup because the femoral head will not fit.

Instead, the circumferential lip 230 is designed so that as the cement displaces out of the acetabular defect, the cement displaces radially from the device 200 at the location of the base 252 of the hemisphere. This thereby ensures that a hemisphere, and only a hemisphere, is being created. Any extra cement can also easily be removed without disrupting the acetabular cement cup being created. The diameter 232 of the circumferential lip 230 varies according to the diameter 222 of the body 220 of the device 200 that is chosen for the specific acetabular defect. The diameter 232 of the circumferential lip 230 varies so that it extends at least 5 mm radially (236 and 238) beyond the diameter 222 of the body 220 at the border of the base 252 of the body 220 circumferentially. Therefore, the diameter 232 of the circumferential lip 230 should be at least the diameter 222 of the body 220 plus at least 10 mm.

One or more elements or aspects or steps, or any portion(s) thereof, from one or more of any of claims 1-26 below can be combined with one or more elements or aspects or steps, or any portion(s) thereof, from one or more of any of the other claims 1-26 or combinations thereof, to form one or more additional implementations and/or claims of the present disclosure.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

While various examples of the present disclosure have been described above, it should be understood that they have been presented by way of example only, and not limitation. Numerous changes to the disclosed examples can be made in accordance with the disclosure herein without departing from the spirit or scope of the invention. Thus, the breadth and scope of the present invention should not be limited by any of the above described examples. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising." Unless otherwise defined, all terms (including technical and scientific terms) used herein have the same meaning as commonly understood by one of ordinary skill in the art to which this invention belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:

1. A device for forming a custom cement cast of an acetabular implant for a patient, the device comprising:
- an elongated handle; and
- a head coupled to a proximal end of the elongated handle, the head comprising:
  - a body having an exterior surface which is shaped as a uniformly spherical cap which is devoid of holes, the body including a circular base and an apex;
  - a circumferential lip extending radially outwardly from the circular base of the body; and
  - a nipple extending from the apex of the body in a direction perpendicular to the circular base;
- wherein the head is configured to release from hardened bone cement.

2. The device of claim 1, wherein the exterior surface of the body of the head between the circumferential lip and the nipple is shaped as an uninterrupted section of a sphere.

3. The device of claim 1, wherein the head is removably coupled to the proximal end of the elongated handle, and wherein the head is selected such that a radius of the body spherical cap is sized to match an acetabular defect of the patient, the radius of the body being a radius of an underlying sphere of the spherical cap.

4. The device of claim 1, wherein a radius of the body is 27.5 mm.

5. The device of claim 1, wherein, in use, the head is pressed into cement in a patient acetabulum, the cement is allowed to harden, and the device is removed from the hardened cement to create an acetabular cement cast having a cement articulation surface.

6. The device of claim 1, wherein a length of the nipple is modifiable to thereby modify a thickness of a cement cast formed between the head and an acetabulum.

7. The device of claim 1, wherein the apex is at a pole of the spherical cap.

8. The device of claim 1, wherein the circumferential lip extends generally along a same plane as the circular base.

9. A system comprising the device of claim 1, wherein the head is removably coupled to the handle and the body has a first spherical size, and wherein the system comprises a second head which may be removably coupled to the proximal end of the elongated handle, the second head comprising a second body having an exterior surface shaped as a uniformly spherical cap which is devoid of holes and configured to release from hardened bone cement, the second body including a circular base and an apex, a second circumferential lip extending radially outwardly from the circular base of the second body, and a second nipple extending from the apex of the second body in a direction perpendicular to the circular base, wherein the second body comprises a second spherical size different than the first spherical size.

10. The device of claim 1, wherein a height of the nipple is 5 mm.

11. The device of claim 1, wherein the nipple is sized and configured to touch both an acetabular bone of the patient and a cement placed between the head and the acetabular bone, and wherein the head is configured to be removed from the cement after the cement hardens thereby forming a hemispherical cement cast in the acetabular bone.

12. The device of claim 11, wherein a thickness of the custom cement cast is the same as a height of the nipple.

13. The device of claim 11, wherein a length of the nipple is sized based on an intended thickness of the custom cement cast.

14. The device of claim 1, wherein the exterior surface of the body is rotationally symmetric such that when cement is in contact with the body, the head is coaxially rotatable around the nipple while the cement hardens without disrupting the cement.

15. The device of claim 1, wherein the body of the head is shaped to match a prosthetic femoral head fitted for the patient.

16. A method for treating an infected total hip arthroplasty in a patient, the method comprising:

removing an implant associated with the infected total hip arthroplasty in the patient;

placing a cement in an acetabulum of the patient;

pressing a device into the cement, thereby forming a concave cement acetabular cast, wherein the device comprises:

an elongated handle; and a head coupled to a proximal end of the elongated handle, the head comprising a body shaped as a spherical cap, a circumferential lip extending radially outwardly from a base of the body, and a nipple extending from an apex of the body in a direction perpendicular to the base, wherein the nipple of the head is a center of rotation of the device whereby the head is coaxially rotatable around the nipple while the cement hardens without disrupting the cement;

advancing the device toward an acetabular bone of the patient until the nipple of the head touches the acetabular bone, thereby ensuring an appropriate thickness of the cement acetabular cast.

17. The method of claim 16, wherein the body of the head is shaped as a hemisphere and includes a circular base.

18. The method of claim 16, wherein a radius of the body is modifiable based on an acetabular defect of the patient, the radius of the body being a radius of an underlying sphere of the spherical cap.

19. The method of claim 16, wherein a length of the nipple is modifiable based on the appropriate thickness of the cement acetabular cast.

20. The method of claim 16, further comprising placing a mineral oil between the cement and the device, thereby preventing the device from adhering to the cement.

21. The method of claim 16, wherein the cement includes an antibiotic bone cement.

22. A method for treating an infected total hip arthroplasty in a patient, the method comprising:

removing an implant associated with the infected total hip arthroplasty in the patient;

placing a cement in an acetabulum of the patient;

selecting a device comprising:

an elongated handle; and a head coupled to an end of the elongated handle, the head comprising a body having an exterior surface which is shaped as a spherical cap and a circumferential lip extending radially outwardly from a base of the body, wherein the head is configured to release from hardened bone cement;

pressing the device head into the cement;

allowing the cement to harden; and removing the device head from the hardened cement, thereby forming a cement cast comprising a cement concave acetabular articulation surface.

23. The method of claim 22, wherein the head comprises a nipple extending from an apex of the body in a direction perpendicular to the base, wherein the nipple of the head is a center of rotation of the device and wherein the exterior surface of the body is rotationally symmetric such that the head is coaxially rotatable around the nipple while the cement hardens without disrupting the cement.

24. The method of claim 22, wherein the head comprises a nipple extending from the body, and wherein the method comprises advancing the device toward an acetabular bone of the patient until the nipple of the head touches the acetabular bone, thereby ensuring an appropriate thickness of the cement acetabular cast.

25. The method of claim 24, wherein the method comprises modifying a length of the nipple to vary a thickness of the cement cast.

26. A device for forming a custom cement cast of an acetabular implant for a patient, the device comprising:

an elongated handle; and a head removably coupled to an end of the elongated handle, the head comprising:

a body having an exterior surface which is shaped as a spherical cap which is devoid of openings, the body including a circular base and an apex;

a circumferential lip extending radially outwardly from the circular base of the body; and wherein the head is configured to release from hardened bone cement and wherein the device is configured such that in use, the head is pressed into cement in a patient acetabulum such that the cement contacts the head, the cement is allowed to harden, and the device is removed from the hardened cement to create an acetabular cement cast having a cement articulation surface shaped by the head.

27. The device of claim 26, wherein the exterior surface of the body is shaped as an uninterrupted section of a sphere.

28. The device of claim 26, wherein the head is removably coupled to the proximal end of the elongated handle, and wherein the head is selected such that a radius of the body spherical cap is sized to match a patient hip joint.

29. The device of claim 26, further comprising a nipple extending from the body in a direction perpendicular to the circular base and wherein, in use, the nipple contacts a patient acetabulum to thereby create a thickness of a cement cast formed between the head and the acetabulum.

30. The device of claim 26, further comprising a nipple extending from the body, and wherein a length of the nipple is modifiable to thereby modify a thickness of a cement cast formed between the head and a patient acetabulum.

31. The device of claim 26, wherein the exterior surface of the head is rotationally symmetric such that when cement is in contact with the body, the head is coaxially rotatable without disrupting the cement.

32. The device of claim 31, wherein the head comprises a nipple extending from an apex of the body in a direction perpendicular to the base, and wherein the nipple is located along a center of rotation of the device.

* * * * *